United States Patent [19]

Stahl

[11] 4,187,177
[45] Feb. 5, 1980

[54] COLUMN FOR HIGH PRESSURE LIQUID CHROMATOGRAPHY

[76] Inventor: Kurt-Wilhelm Stahl, Bischofsholer Damm 116, 3000 Hanover 1, Fed. Rep. of Germany

[21] Appl. No.: 957,517

[22] Filed: Nov. 3, 1978

[51] Int. Cl.² .............................................. B01D 15/08
[52] U.S. Cl. .................... 210/198 C; 210/287
[58] Field of Search ................. 210/31 C, 198 C, 287; 55/386

[56] References Cited

U.S. PATENT DOCUMENTS 4,093,550  6/1978  Stahl et al. ..................... 210/198 C Primary Examiner—John Adee
Attorney, Agent, or Firm—Donald D. Jeffery

[57] ABSTRACT

In a column for high pressure liquid chromatography (HPLC) having a tube filled with sorbent for the passage of a solvent medium and samples to be analyzed, and a pressure jacket concentrically surrounding said tube, so that an annular interspace is provided which is filled with the solvent medium fed under pressure and in which the pressure can be equal or higher to the pressure within the internal tube, both ends of the interspace are sealed by means of packings surrounding the internal tube like stuffing boxes, and the ends of the internal tube are provided with perforated stoppers, which extend with a stud-like elongation into the internal tube to the region which is surrounded by the respective packing, so that the elongation support the wall of the internal tube against the sealing pressure of the packings. Accordingly, the internal tube can be a thin-walled glass column or even a hose of flexible plastics. Furthermore, at the inlet end of the column a valve is provided for adjusting the pressure within the internal tube with respect to the pressure within the interspace.

13 Claims, 1 Drawing Figure

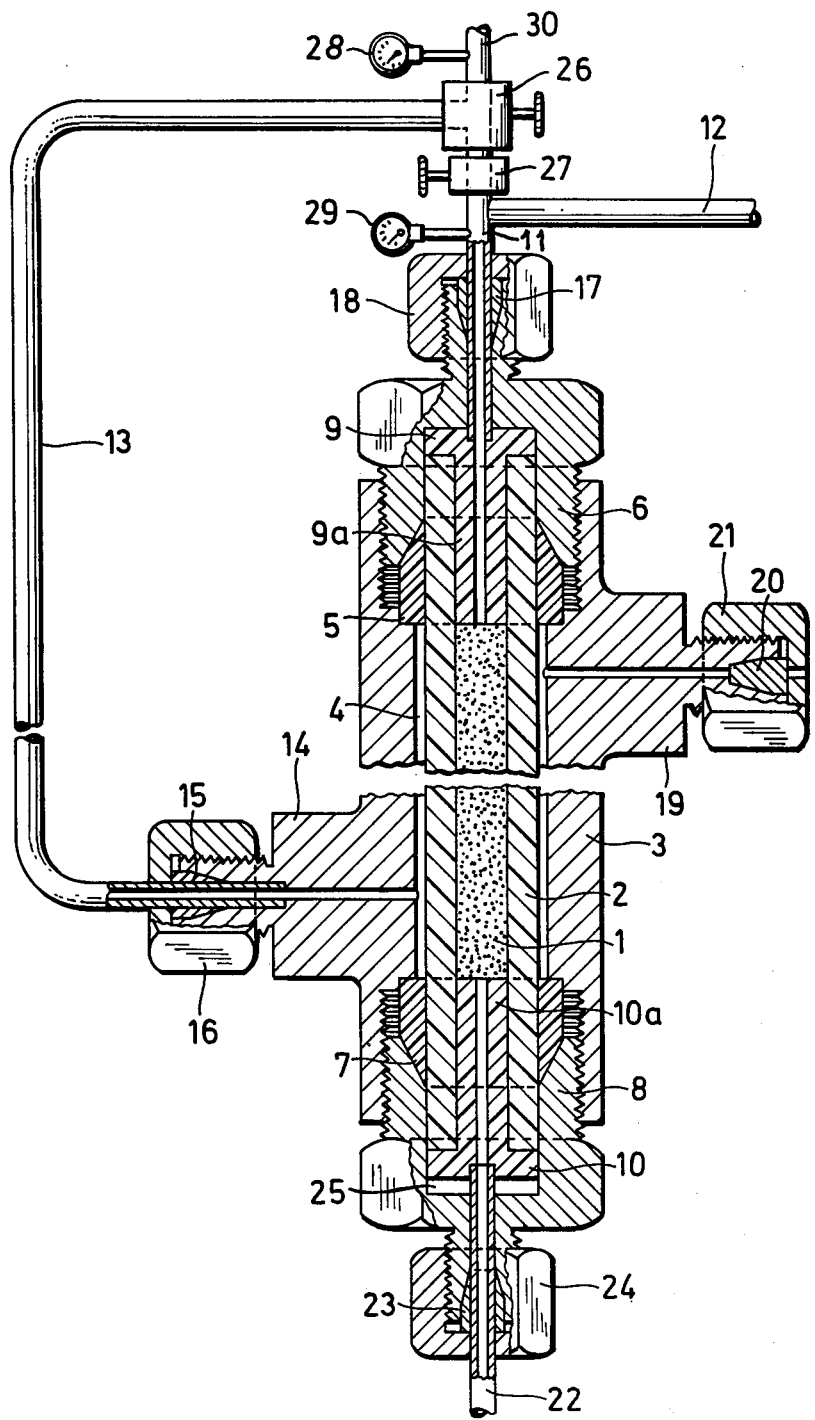

COLUMN FOR HIGH PRESSURE LIQUID CHROMATOGRAPHY

The invention relates to a column for high pressure liquid chromatography (HPLC) having an internal tube filled with sorbent for the passage of solvent medium and samples to be analysed concentrically surrounded by a pressure jacket so that an annular interspace between said internal tube and said pressure jacket is provided, which interspace is sealed at both ends of the column and is filled with the same solvent medium which is fed by a pumping means under pressure to the internal tube, the pressure in the interspace being equal to the pressure of the solvent medium flowing to the column.

In U.S. Pat. No. 4,093,550, a column for HPLC is disclosed wherein the packings sealing the ends of the interspace bear against the internal tube in a region where it is filled with sorbent. Accordingly, the wall of the internal tube must have a sufficient thickness and must be sufficiently rigid to resist the radial sealing pressure with which the packings are pressed against the internal tube. Furthermore, the pressure within the interspace is always substantially equal to the pressure within the internal tube so that it is not possible to use in such known columns dry-filled internal tubes of plastic material.

The object of the invention is to provide an improved column for HPLC which can be used with thin-walled internal tubes of glass or with an internal tube made of a hose of flexible plastics which can be filled outside the column and need not to have a precise length.

A further object of the invention is to provide a column for HPLC in which the pressure exerted onto the outer wall of the internal tube through the interspace can be raised for at least a short time before starting the chromatographic operation of the column considerably above the pressure within the internal tube so that also internal tubes made of flexible plastics filled loosely with dry-packed sorbent can efficiently be used for higher efficient liquid chromatography.

The column for high pressure liquid chromatography (HPLC) of the present invention has at least at the inlet end and preferably at the inlet and at the outlet end of the internal tube a stopper provided with a stud-like elongation extending into said internal tube to the region which is surrounded by the respective packing, said elongation supporting the wall of said internal tube against the sealing pressure of said packing. The stoppers and their elongation are provided with an axial bore through which the solvent medium and samples fed to said medium can flow. However, the wall thickness of the elongation is sufficient to resist the sealing pressure of the respective packing, so that the internal tube can be a hose made of flexible plastics or a thin-walled glass column. The stoppers can comprise of plastics or of stainless steel or other suitable material.

With an arrangement of this type, i.e. a mobile phase (sorbent medium) locked liquid chromatographic column, the ends of the interspace can effectively be sealed without the risk of damaging the internal tube or reducing the internal cross-section of said tube by the sealing pressure. Consequently, the internal tube can be made of relatively inexpensive material, so that it can be disposed after a single use.

The present invention further provides a column for high pressure liqud chromatography (HPLC) which is provided near the inlet end for the solvent medium and the samples with means for adjusting the flow resistance before the inlet end of the internal tube so that the pressure within the internal tube can be lower than the pressure within the interspace. This is of crucial interest when a dry-packed hose of flexible plastics is used as internal tube. In this case the loose column bed has to be transformed into a tight or dense form prior to starting the operation of the column for analysis in order to obtain efficient chromatographic results which means that the pressure in the interspace should be considerably higher than the pressure within the internal tube. For chromatographic operation the pressures within the interspace and the internal tube can be continuously re-equalized by means of an infinitely variable throttle valve. The pressures can be indicated by means of pressure indicators like pressure gauges arranged upstream and downstream of said flow resistance adjusting means.

A column for high pressure liquid chromatography (HPLC) having the aforesaid construction has important advantages. The mobile liquid phase locked construction is simple and enables the use of cheap and disposable thin-walled and/or plastic internal tubes without the risk that if the internal tube is pressurized by an external gas source gas under elevated pressure can penetrate through the plastics wall into the internal tube, can dissolve in the mobile liquid phase and can seriously disturb the chromatographic analysis in sensible detector systems. Owing to the simple construction and the rapid exchangeability of the internal tube, tubes pre-packed with sorbent of all kind, i.e. so called prefabricated columns, especially columns with standardized separation effect, can be used. The wall thickness of such internal tubes can be for example less than 1 mm while the outer diameter could be as large as up to 11 mm.

When stoppers with a stud-like elongation are used at both ends of the internal tube, said internal tube can be made also of plastics and especially soft or flexible plastics. Using plastics as material for the internal tube allows tightening of columns loosely-filled with small diameter particles (10 micron) which for economic reasons have been pre-filled in a dry manner and not by the chromatographically effective but expensive wet "pressure filtration" technics.

For the internal tube resins or plastics of different kind can be used. The most preferred plastics are, however, polymers of halogene fluoro hydrocarbons like polytetrafluoroethylene (PTFE) or low chlorinated PTFE (PCTFE). However, it is also possible to use polyethylene or polypropylene as material for the internal tube which depends on the requirements of the solvent to the chemical resistance of the material of the internal tube.

Also in view of the mechanical properties of the internal tube different materials can be used, i.e. brittle and relatively rigid resins as well as relatively soft types of resins.

The invention will now be described with reference to the drawing illustrating by way of example a preferred embodiment of the column in a partially shown longitudinal section.

Referring to the single figure of the drawings, a sorbent 1 is filled into an internal tube 2 such as a glass column which is arranged within a pressure jacket 3 so that an annular interspace 4 filled with the liquid phase (liquid solvent) is provided between the internal tube 2 and the pressure jacket 3.

A packing 5 surrounding the internal tube 2 near its inlet end is pressed against the wall thereof and against the pressure jacket 3 by a screw 6 screwed into the pressure jacket 3. In the same manner, the interspace 4 is sealed at the outlet end of the internal tube 2 by a packing 7 and a screw 8. Packings 5 and 7 are made of polytetrafluoroethylene (PTFE). In the drawing the cooperating pressing surfaces of the packings 5 and 7 and of the screws 6 and 8 are conical.

The internal tube 2 is closed by two perforated stoppers 9 and 10 made of polytetrafluoroethylene which serve mechanically to confine the sorbent 1 to the internal tube, to center capillaries 11 and 22 and to stabilize the internal tube against the sealing pressure of the packings 5 and 7. Column inlet capillary 11, having for example an outer diameter of 1/16", opening into the stopper 9 is used for the introduction of a solvent medium and samples, which are fed to the solvent through a sample feeding line 12 connected to the column inlet capillary 11. Above the sample feeding line 12 an interspace feeding line 13 is branched off from the medium feeding line 30, connected to a pumping means (not shown) delivering the solvent medium with the desired pressure. The interspace feeding line 13 is in communication with the lower end of the interspace 4 by a short pipe 14 laterally welded to the pressure jacket 3.

The pressure compensating interspace feeding line 13 is sealed with respect to the short pipe 14 by a sealing cone 15 of metal and a union nut 16. In similar manner, column inlet capillary 11 is sealed with respect to the screw 6 by a sealing cone 17 and a union nut 18. At the upper end of the interspace 4 is welded to the pressure jacket 3, on the side opposite to the short pipe 14, a vent pipe 19, which is sealed by a nut-like perforated closing cap 21, via a dummy seal 20. Thus, when the column is in operation the interspace 4 can be vented or the pressure within it can be released and flushed in a few seconds.

The stopper 10 closing the lower end of the internal tube 2 is also perforated and centers the column discharge capillary 22 which can be shifted with respect to screw 8 by a coneshaped packing 23 and a union nut 24. The packing 23 can be made of polytetrafluoroethylene.

A tolerance space 25 between stopper 10 and screw 8 serves to compensate differences in length between the internal tube 2 and the pressure jacket 3. The tolerance space 25 is bridged by the discharge capillary 22 and thus cannot have an adverse effect on the chromatographic measurement. Sealing screws 6 and 8 may have opposed threads, i.e. one a lefthand thread and the other one a righthand thread.

Stoppers 9 and 10 are each provided with a stud-like elongation 9a and 10a, respectively, extending into the internal tube 2 as deep as that it supports the wall of the internal tube 2 against the external pressure of the packings 5 and 7, so that they stabilize the internal tube 2 against the sealing pressure of packings 5 and 7 and the internal tube 2 can accordingly be a relatively thin-walled glass column or a hose of flexible plastics material. The elongations 9a and 10a are integral with the respective stoppers 9 and 10 which can be made of plastics or stainless steel.

A three-way valve 26 is provided which connects the column inlet capillary 11 and also the interspace feeding line 13 to the medium feeding line 30. If valve 26 is in such a position that medium feeding line 30 is connected only to interspace feeding line 13 while the inlet to column inlet capillary 11 is closed, the pressure of the pumping device of the mobile phase acts only onto the outer surface of the internal tube 2 through interspace 4 pressurizing the dry-filled plastics internal tube to give a dense or tight column packing before chromatographic operation for analytical purposes is started. This operation is started by opening the connection of valve 26 to the inlet of column inlet capillary 11 without closing the connection to interspace feeding line 13 so that the pressure in the interspace 4 is equal to the inlet pressure of column during operation.

As an alternative to valve 26 a throttle valve 27 is arranged between medium feeding line 30 and column inlet. In this case, interspace feeding line 13 is branched off from medium feeding line 30 upstream throttle valve 27 while sample feeding line 12 is connected to column inlet capillary downstream valve 27. In this embodiment, a tightening or partly closing of throttle valve 27 during the pre-operational stage creates a flow resistance upstream the inlet end of the column resulting in an interspace pressure higher than the pressure in the internal tube which can be regulated in an infinitely variable manner so that a pressure difference between the interspace and the internal tube is maintained for a given period prior to operation of the column.

In any case, it is possible by means of three-way valve 26 or throttle valve 27 to elevate the pressure outside the internal tube 2 above the pressure inside the internal tube 2. To show the pressure difference and to adjust valve 27 and/or the pumping device accordingly, two pressure sensors and indicators 28 and 29 like pressure gauges are provided, one being arranged upstream and the other being arranged downstream of throttle valve 27.

What I claim is:

1. A column for high pressure liquid chromatography (HPLC), having a feed line for a solvent medium, a tube filled with sorbent for the passage of said solvent medium and samples to be analysed, said tube comprising an inlet and an outlet end each closed by a perforated stopper, and being concentrically surrounded by a pressure jacket so that an annular interspace between said tube and said pressure jacket is provided, one end of said interspace being connected through a separate line with the feed line through which said solvent is fed under pressure through an inlet capillary to the internal tube so that the pressure in the interspace can be equal to the pressure at the inlet end of said internal tube, both ends of said interspace being sealed by means of packings surrounding said internal tube, venting means connected to the other end of the interspace, and means for adjusting the flow resistance in the inlet capillary of said internal tube, said adjusting means being arranged upstream of the inlet end of said internal tube and downstream of where said separate line connects said interspace with said feed line.

2. A column as claimed in claim 1, wherein said flow resistance adjusting means is an infinitely variable throttle valve.

3. A column as claimed in claim 2, further including pressure indicating means connected upstream and downstream of said throttle valve relative to the solvent medium feed line and the capillary connected to the inlet end of the internal tube, respectively.

4. A column as claimed in claim 2, wherein said valve is a three-way valve interconnecting said separate line to said interspace and said inlet capillary connected to the inlet end of the internal tube.

5. A column as claimed in claim 4, wherein pressure indicating means are arranged upstream and downstream of said three-way valve.

6. A column for high pressure liquid chromatography (HPLC), having a feed line for a solvent medium, a tube filled with sorbent for the passage of said solvent medium and samples to be analysed, said tube comprising an inlet and an outlet end each closed by a perforated stopper, and being concentrically surrounded by a pressure jacket so that an annular interspace between said tube and said pressure jacket is provided, one end of said interspace being connected through a separate line with said feed line through which said solvent medium is fed under pressure to the internal tube so that the pressure in the interspace can be equal to the pressure at the inlet end of said internal tube, both ends of said interspace being sealed by means of packings surrounding said internal tube, venting means connected to the other end of the interspace, means for adjusting the flow resistance in the inlet capillary of said internal tube, said adjusting means being arranged upstream of the inlet end of said internal tube and downstream of where said separate line connects said interspace with said feed line, a sample feeding line connected to said feed line, and wherein the stopper at the outlet end of the internal tube is provided with a stud-like elongation extending into said internal tube to the region which is surrounded by the adjacent packing, said elongation supporting the wall of said internal tube against the sealing pressure of said packing.

7. A column as claimed in claim 6, wherein the stopper at the inlet end of the internal tube is similarly provided with a stud-like elongation extending into said internal tube to the region which is surrounded by the adjacent packing, said elongation supporting the wall of said internal tube against the sealing pressure of said packing.

8. A column as claimed in claim 6, wherein said internal tube is a hose made of flexible plastic material.

9. A column as claimed in claim 6, wherein said stoppers are made of plastic material.

10. A column as claimed in claim 6, wherein said stoppers are formed of stainless steel.

11. A column as claimed in claim 1, wherein said internal tube is a hose made of flexible plastic material.

12. A column as claimed in claim 1, wherein said stoppers are formed of plastic material.

13. A column as claimed in claim 1, wherein said stoppers are formed of stainless steel.

* * * * *